United States Patent
Rybak

(10) Patent No.: US 7,622,458 B2
(45) Date of Patent: Nov. 24, 2009

(54) COMBINATION OF ET-743 AND A 5-FLUOROURACIL PRO-DRUG FOR CANCER TREATMENT

(75) Inventor: Mary Ellen Rybak, Princeton, NJ (US)

(73) Assignee: Pharma Mar, S.A.U., Madrid (ES)

( * ) Notice: Subject to any disclaimer, the term of this patent is extended or adjusted under 35 U.S.C. 154(b) by 0 days.

(21) Appl. No.: 10/579,160

(22) PCT Filed: Nov. 15, 2004

(86) PCT No.: PCT/GB2004/050026

§ 371 (c)(1),
(2), (4) Date: Mar. 1, 2007

(87) PCT Pub. No.: WO2005/049031

PCT Pub. Date: Jun. 2, 2005

(65) Prior Publication Data

US 2007/0190164 A1    Aug. 16, 2007

(51) Int. Cl.
A01N 43/04 (2006.01)
A61K 31/70 (2006.01)

(52) U.S. Cl. .............................. 514/50; 514/43; 514/49

(58) Field of Classification Search .................... None
See application file for complete search history.

(56) References Cited

U.S. PATENT DOCUMENTS

| | | | |
|---|---|---|---|
| 5,089,273 | A | 2/1992 | Rinehart et al. |
| 5,149,804 | A | 9/1992 | Rinehart et al. |
| 5,256,663 | A | 10/1993 | Rinehart et al. |
| 5,472,949 | A | 12/1995 | Arasaki et al. |
| 5,478,932 | A | 12/1995 | Rinehart et al. |
| 5,552,544 | A | 9/1996 | Fernandez et al. |
| 5,654,426 | A | 8/1997 | Rinehart et al. |
| 5,721,362 | A | 2/1998 | Corey et al. |
| 5,908,835 | A | 6/1999 | Bissery |
| 5,985,876 | A | 11/1999 | Rinehart et al. |
| 6,124,293 | A | 9/2000 | Rinehart et al. |
| 6,153,590 | A | 11/2000 | Andersen et al. |
| 7,241,892 | B1 | 7/2007 | Cuevas et al. |
| 2002/0137663 | A1 | 9/2002 | Forman et al. |
| 2004/0002602 | A1 | 1/2004 | Francesch et al. |
| 2004/0019027 | A1 | 1/2004 | Forman et al. |
| 2004/0108086 | A1 | 6/2004 | Takahashi et al. |
| 2006/0030571 | A1 | 2/2006 | Rinehart |
| 2006/0094687 | A1 | 5/2006 | Beijnen |
| 2007/0004691 | A1 | 1/2007 | Donald |
| 2007/0082856 | A1 | 4/2007 | Gianni |
| 2007/0128201 | A1 | 6/2007 | D'Incalci et al. |

FOREIGN PATENT DOCUMENTS

| WO | WO 99/51238 | 10/1999 |
|---|---|---|
| WO | WO 99/58125 | 11/1999 |
| WO | WO 00/69441 | * 11/2000 |
| WO | WO 00/69862 | 11/2000 |
| WO | WO 01/77115 | 10/2001 |
| WO | WO 01/87894 | 11/2001 |
| WO | WO 02/36135 A2 | 5/2002 |
| WO | WO 02/064843 | 8/2002 |
| WO | WO 03/020259 | 3/2003 |
| WO | WO 03/039571 A1 | 5/2003 |
| WO | WO 2005/049029 | 6/2005 |
| WO | WO 2005/049030 | 6/2005 |
| WO | WO 2005/049031 | 6/2005 |
| WO | WO 2006/035244 | 4/2006 |
| WO | WO 2006/046080 | 5/2006 |

OTHER PUBLICATIONS

Ishikawa et al. Biochemical Pharmacology (1998), vol. 55, pp. 1091-1097.*
Naoto Takahashi et al. "Sequence-dependent Synergistic Cytotoxicity of Ecteinascidin-743 and Paclitaxel in Human Breast Cancer Cell Lines in Vitro and in Vivo," Cancer Research, No. 62, pp. 6909-6915 (Dec. 1, 2002).
U.S. Appl. No. 09/546,877, filed Apr. 10, 2000, Rinehart.
U.S. Appl. No. 09/787,461, filed Mar. 2, 2001, Cvitkovich et al.
U.S. Appl. No. 10/416,086, filed Sep. 17, 2003, Takahashi et al.
U.S. Appl. No. 10/492,320, filed Oct. 21, 2002, Jimeno et al.
U.S. Appl. No. 10/524,152, filed Aug. 13, 2003, Esteban et al.
U.S. Appl. No. 10/540,092, filed Dec. 18, 2003, Iglesias et al.
U.S. Appl. No. 10/558,133, filed Nov. 15, 2006, D'Incalci et al.
U.S. Appl. No. 10/575,132, filed Oct. 14, 2004, Donald et al.
U.S. Appl. No. 10/579,130, filed May 12, 2006, Rowinsky et al.
U.S. Appl. No. 10/579,251, filed Oct. 20, 2006, Gianni et al.
U.S. Appl. No. 11/132,466, filed May 18, 2005, Rinehart et al.
U.S. Appl. No. 11/261,876, filed Oct. 28, 2005, Beijnen et al.
U.S. Appl. No. 11/576,115, filed Sep. 28, 2005, Allavena et al.
U.S. Appl. No. 11/577,790, filed Apr. 23, 2007, Gilles et al.
U.S. Appl. No. 11/769,873, filed Jun. 28, 2007, Cvitkovich et al.
Akers, "Excipient -Drug Interactions in Parenteral Formulations," Journal of Pharmaceutical Sciences, 91(11), pp. 2283-2300, Nov. 2002.
Barrera, H. et al., "Interaction of ET-743 and standard cytotoxic agents against a panel of human tumor cell lines," Proceedings of the American Association for Cancer Research, vol. 40, p. 591, Abstract No. 3896, Mar. 1999.
Biroccio et al., "Telomere Dysfunction Increases Cisplatin and Ecteinascidin-743 Sensitivity of Melanoma Cells," Molecular Pharmacology, 63:632-638 (2003).
Blay et al., "Combination of Trabectedin and Doxorubicin for the Treatment of Patients with Soft Tissue Sarcoma: Safety and Efficacy Analysis," 43$^{rd}$ annual ASCO meeting, Jun. 1-5, 2007.

(Continued)

Primary Examiner—Patrick T Lewis
(74) Attorney, Agent, or Firm—Kenneth H. Sonnenfeld; Michael A. Willis; King & Spalding LLP

(57) ABSTRACT

Methods of treating a human body for cancer are provided. In one aspect, a therapeutic amount of capecitabine is administered in combination with ET-743 in a dose range between 0.75 and 1.4 mg/m$^2$ for Et-743. In a related aspect, an effective therapeutic amount of ET-743 is administered in combination with capecitabine in a dose range between 1500 to 2500 mg/m/day for capecitabine.

26 Claims, No Drawings

OTHER PUBLICATIONS

Bonfanti et al., "Effect of Ecteinascidin-743 on the Interaction Between DNA Binding Proteins and DNA," Anticancer Drug Des. 14, 179-86, 1999.

Bowman, A. et al., "Phase I clinical and pharmacokinetic (PK) study of ecteinascidin-743 (ET-743) given as a one hour infusion every 21 days," Annals Oncology, Abstract 452, 1998.

Brandon et al., In-vitro Cytotoxicity of ET-743 (Trabectedin, Yondelis), a Marine Anti-cancer Drug, in the Hep G2 Cell Line: Influence of Cytochrome P450 and Phase II Inhibition, and Cytochrome P450 Induction, Anti-cancer Drugs, 16:935-943 (2005).

Burstein et al., "Phase I study of Doxil and Vinorelbine in Metastatic Breast Cancer," Annals of Oncology, vol. 10, pp. 1113-1116, 1999, XP8086751.

European Agency for the Evaluation of Medicinal Products, "Committee for Proprietary Medicinal Products Summary of Opinion for Yondelis", Nov. 20, 2003.

Corey et al., "Enantioselective Total Synthesis of Ecteinascidin 743", J. Am. Chem. Soc., 118, 9202-9203, 1996.

Cvitkovic, E. et al., "Final results of a phase I study of ecteinascidin-743 (ET-743) 24 hour (h) continuous infusion (CI) in advanced solid tumors (AST) patients (pts)," 1999 ASCO Annual Meeting Proceedings, Abstract No. 690, May 15-18, 1999.

Cvitkovic, E. et al., "Ecteinascidin-743 (ET-743) 24 hour continuous intravenous infusion (CI) phase I study in solid tumors (ST) patients," Annals Oncology, Abstract 456, 1998.

Delaloge, S. et al., "Ecteinascidin-743: A Marine-Derived Compound in Advanced Pretreated Sarcoma Patients-Preliminary Evidence of Activity", J. of Clinical Oncology, vol. 19, No. 5, pp. 1248-1255, 2001.

DeVita et al., "Combination Versus Single Agent Chemotherapy: A Review of the Basis for Selection of Drug Treatment of Cancer", Cancer, vol. 35, pp. 98-110, 1975.

D'Incalci et al., "The Combination of ET-743 and Cisplatin (DDP): From a Molecular Pharmacology Study to a Phase I Clinical Trial," from the AACR Annual Meeting of Apr. 6-10, 2002, Abstract 404.

D'Incalci et al., "Preclinical and Clinical Results with the Natural Marine Product ET-743," Expert Opin. Investig. Drugs, 12(11):1843-1853 (2003).

D'Incalci et al., "In human tumor xenografts the resistance to ET-743 or to cisplatin can be overcome by giving the two drugs in combination," European Journal of Cancer, 38, Suppl. 7, 34 (Nov. 2002).

D'Incalci et al., "The combination of yondelis and cisplatin is synergistic against human tumor xenografts," European Journal of Cancer 39: 1920-1926 (2003).

Donald et al., "Complete Protection By High-Dose Dexamethasone Against The Hepatotoxicity of the Novel Antitumor Drug Yondelis (ET-743) in The Rat," Cancer Research, vol. 63, p. 5902-5908, Sep. 2003.

Donald et al., "Dietary Agent Indole-3-Carbinol Protects Female Rats Against the Hepatotoxicity of the Antitumor Drug ET-743 (trabectidin) Without Compromising Efficacy in a Rat Mammary Carcinoma" International Journal Of Cancer, vol. 111, No. 6, p. 961-967, 2004.

Dorr and Van Hoff, "Doxorubicin," Cancer Chemotherapy Handbook, 1994, pp. 395-416.

"Doxil (doxorubicin Hcl Liposome Injection) Product Information", Oct. 10, 2004, pp. 1-16, XP002389462, <<web.archive.org/web/20041009180>>.

Drugs Fut., "Ecteinascidin-743" vol. 22, No. 11, p. 1279, 1997.

Eckhardt et al., "In vitro Studies of a Novel Marine Cytotoxic, Ecteinascidin (ET-743)," New Drugs and Pharmacology, Annals of Oncology, 7 (Suppl. 5), 131, Abstract 632P (1996).

Endo et al., "Total Synthesis of Ecteinascidin 743", J. Am. Chem. Soc., 124, 6552-6554, 2002.

Erba et al., "Synergistic cytotoxic effect of ET-743 and cisplatin," Clinical Cancer Research, vol. 6, Abstract 209 (Nov. 2000).

Erba et al., "Combination of yondelis (ET-743) and oxaliplatin in experimental ovarian cancer," from the AACR-NCI-EORTC International Conference on Molecular Targets and Cancer Therapeutics of Nov. 17-21, 2003, Abstract C247.

Erba et al., "ET-743 and Cisplatin (DDP) Show in Vitro and in Vivo Synergy Against Human Sarcoma and Ovarian Carcinoma Cell Lines," from the AACR-NCI-EORTC Conference on Molecular Targets and Cancer Therapeutics of Oct. 29 -Nov. 2, 2001, Abstract 406.

Erlichman, C., "18: Pharmacology of Anticancer Drugs," The Basic Science of Oncology, 2nd edition, Tannock et al., editors, McGraw-Hill, New York, pp. 317-337, 1992.

FDA approved label for Pharmacia and Upjohn's Doxorubicin Hydrochloride for Injection (May 8, 2003).

Faircloth et al., "In Vivo Combinations of Chemotherapeutic Agents with Ecteinascidin 743 (ET743) Against Solid Tumors," from the Proceedings AACR-NCI-EORTC of Nov. 2001, Abstract 387.

Faircloth et al., "Dexamethasone Potentiates the Activity of Ecteinascidin 743 in Preclinical Melanoma and Osteosarcoma Models," Abstract and Presentation 379 (2002).

Faulkner et al., "Symbiotic Bacteria in Sponges: Sources of Bioactive Substances," Drugs from the Sea, Fusetani, N. (ed.), Basel Karger, 2000, pp. 107-119.

Fayette et al., "ET-743: a Novel Agent with Activity in Soft-Tissue Sarcomas," Current Opinion in Oncology, 18:347-353 (2006).

Fourouzesh, B. et al., "Phase I and pharmacokinetic study of the marine-derived DNA minor groove binder ET-743 on a weekly x3 every-4-week schedule in patients with advanced solid malignancies," Proceedings of the 2001 AACR-NCI-EORTC International Conference, Abstract No. 209, Oct. 29-Nov. 2, 2001.

Fourouzesh, B. et al., "Phase I and pharmacokinetic study of ET-743, a minor groove DNA binder, administered weekly to patients with advanced cancer," Proc Am Soc Clin Oncol, vol. 20, 2001 ASCO Annual Meeting Proceedings, Abstract No. 373, 2001.

Forouzesh, B., et al., "Phase I and pharmacokinetic study of ET-743, a minor groove DNA binder, administered weekly to patients with advanced cancer," European Journal of Cancer, ECCO 11, vol. 37, supplement 6, Abstract No. 106, Oct. 21-25, 2001.

Friereich et al., "Quantitative Comparison of Toxicity of Anticancer Agents in Mouse, Rat, Hamster, Dog, Monkey, and Man," Cancer Chemotherapy Reports, 50:4, May 1966, pp. 219-245.

Fukuyama et al., "Total Synthesis of Saframycin A," J. Am. Chem. Soc., 112, 3712-3713, 1990.

Fukuyama et al., "Stereocontrolled Total Synthesis of Saframycin B," J. Am. Chem. Soc., 104, 4957-4958, 1982.

Garcia Gravalos, M.D., et al., "In vitro schedule-dependent cytotoxicity by ecteinascidin 743 (ET-743) against human tumor cells," 23rd European Society for Medical Oncology Congress, Abstract No. 652, Nov. 6-10, 1998.

Ghielmini, M. et al., "Schedule-dependent myelotoxicity induced in vitro by the new marine derived minor groove interacting agent ecteinascidin 743," ECCO, vol. 9, Abstract No. 807, Sep. 17, 1997.

Ghielmini, M. et al., "In vitro schedule-dependency of myelotoxicity and cytotoxicity of Ecteinascidin 743 (ET-743)," Annals of Oncology, vol. 9, pp. 989-993, 1998.

Gianni et al. "Definition of the Least Toxic Sequence and Optimal Therapeutic Dose of Yondelis® in Combination with Doxorubicin in Patients with Untreated Metastatic Soft Tissue Sarcomas and Advanced Pre-Treated Anthracycline," Clinical Cancer Research, vol. 9, No. 16, p. 6081S (Dec. 2003).

Goodman & Gilman's The Pharmaceutical Basis of Therapeutics, p. 36, 1975.

Goodman & Gilman's The Pharmaceutical Basis of Therapeutics ($9^{th}$ edition), p. 930, 1996.

Goodman & Gilman's The Pharmaceutical Basis of Therapeutics ($9^{th}$ edition), pp. 1230. 1232, 1996.

Gore et al., "Phase I Combination Study of Trabectedin and Capecitabine in Patients With Advanced Malignancies," Poster Presentation, 42nd ASCO Annual Meeting held on Jun. 2-6, 2006, Atlanta, Georgia.

Grever et al., "The National Cancer Institute: Cancer Drug Discovery and Development Program", Seminars in Oncology, vol. 19, No. 6, 622-638, Dec. 1992.

Grosso et al., "Steroid Premedication Markedly Reduces Liver and Bone Marrow Toxicity of Trabectedin in Advanced Sarcoma," European Journal of Cancer 42:10, 1484-1490 (2006).

Gurtler, J.S. et al., "Trabectedin in third line breast cancer: a multicenter, randomized, phase II study comparing two administration regimens," Journal of Clinical Oncology, 2005 ASCO Annual Meeting Proceedings, vol. 23, No. 16S, part I of II (Jun. 1 Supplement), Abstract No. 625, 2005.

Hendriks, H.R. et al., "High antitumor activity of ET743 against human tumor xenografts from melanoma, non-small-cell lung and ovarian cancer," Annals of Oncology, vol. 10, pp. 1233-1240, 1999.

Hidalgo, M., et al., "A phase I and pharmacokinetic (PK) study of ET-743, a novel minor groove binder of marine origin administered on a daily×5 schedule," 23rd European Society for Medical Oncology Congress, Abstract No. 613P, Nov. 6-10, 1998.

Hillebrand, M.J.X. et al., "Pharmacokinetics of ecteinascidin-743 (ET-743) in three phase I studies," Annals Oncology, Abstract No. 455, 1998.

Holmes, "Paclitaxel Combination Therapy in the treatment of Metast Breast Cancer: A Review," Seminars in Oncology, vol. 23, pp. 46-56, 1996.

Hornicek et al., "Effect of Ecteinascidin-743 and Plasminogen related Protein B on a Human Chondrosarcoma Xenograft Tumor in Mice," Clinical Cancer Research, vol. 7 Supplement P3734S-3734S, Abstract 398 (Nov. 2001).

Izbicka, E. et al., "In vitro antitumor activity of the novel marine agent, Ecteinascidin-743 (ET-743, NSC- 648766) against human tumors explanted from patients," Annals of Oncology, vol. 9, pp. 981-987, 1998.

Jimeno, J.M. et al., "Enhancing the preclinical in vivo antitumor activity of ecteinascidin 743, a marine natural product currently in phase II clinical trials," Proceedings of the 1999 AACR-NCI-EORTC International Conference, Clinical Cancer Research, vol. 5, Abstract No. 306, Nov. 1999.

Jimeno, J. et al., "Phase I and pharmacokinetic (PK) study of Et-743, a novel minor groove binder of marine origin on a daily [times] 5 schedule," 1998 ASCO Annual Meeting Proceedings, Abstract No. 737, 1998.

Jimeno, Jose et al., "Adding Pharmacogenomics to the Development of New Marine-Derived Anticancer Agents," Journal of Translational Medicine, vol. 4, issue 3, Jan. 9, 2006, downloaded from the internet website: <<http://www.translational-medicine.com/content/4/1/3>>.

Jin, et al., Ecteinascidin-743, A Transcription-Targeted Chemotherapeutic that Inhibits MDR I Activation. Proc. Natl. Acad. Sci. USA, 97, 6775-9, 2000.

Kanzaki et al., "Activity of Ecteinascidin 743 and Synergism with Doxorubicin and Vincristine in P-Glycoprotein/MDR1 Over-Expression Cell Lines," from the Proceedings of the AACR, vol. 42, Abstract 4354 (Mar. 2001).

Kanzaki et al., "Microsatellite Instability (MSI) Induced by Ecteinascidin743 and Protection with Aspirin," from the 93rd Annual Meeting of the American Association for Cancer Research, Abstract 5382 (Apr. 6-10, 2002), vol. 43, Mar. 2002, p. 1087.

Kovalcik et al., "The Stability of Cyclophosphamide in Lyophilized Cakes. part I. Mannitol, Lactose, and Sodium Biocarbonate as Excipients," Journal of Parenteral Science and Technology, vol. 42, No. 1, Jan.-Feb. 1988, pp. 29-37.

Laverdiere et al., "Phase II Study of Ecteinascidin 743 In Heavily Pretreated Patients with Recurrent Osteosarcoma", Cancer, American Cancer Society, Philadelphia, PA, Aug. 15, 2003, vol. 98:4, pp. 832-840, XP002314512.

Leonetti et al., "Antitumoral Effect of the G-quadraplex Interactive Compound RHPS4 on Human Melanoma Cells Possessing Relatively Long Telomeres," from the Proceedings of the AACR, vol. 45, Mar. 2004.

Lyass et al., "Phase I Study of Doxil-Cisplatin Combination Chemotherapy in Patients with Advanced Malignancies," Clinical Cancer Research, vol. 7, pp. 3040-3046, Oct. 2001, XP8086753.

Maier et al., "In vitro inhibition of endothelial cell growth by the antiangiogenic drug AGM-1470 (TNP-470) and the antiendoglin antibody TEC-11," Anti-Cancer Drugs, vol. 8, pp. 238-244, 1997.

Magro et al., "The Role of PARP and PARP Inhibitors in Yondelis (Trabectedin) Mediated Cytotoxicity," Abstract and Presentation from the AACR Annual Meeting, Apr. 17, 2007.

Manzanares et al., "Advances in the Chemistry and Pharmacology of Ecteinascidins, A Promising New Class of Anticancer Agents," Curr. Med. Chem.— Anti-Cancer Agents, 2001, vol. 1, pp. 257-276.

Martinez, et al., Phthalascidin, A Synthetic Antitumor Agent with Potency and Mode of Action Comparable to Eeteinaseidin 743. Proc. Natl. Acad. Sci. USA 96; 3496-501, 1999.

Martinez, E. J. et al., A New, More Efficient, and Effective Process for the Synthesis of a Key Pentacyclic Intermediate for Production of Ecteinascidin and Phthalascidin Antitumor Agents. Org. Lett. 2, 993-6, 2000.

Menchaca et al., "Synthesis of Natural Ecteinascidins (ET-729, ET-745, ET-759B, ET-736, ET-637, ET-594) from Cyanosafracin B," J. Org. Chem., published on web Oct. 21, 2003, pp. 8859-8866.

McLeod, "Clinically relevant drug-drug interactions in oncology," Br. J. Clin. Pharmacol., 45:539-544 (1998).

McMeekin, D.S. et al., "Final results of a phase II study of weekly trabectedin in second/third line ovarian carcinoma," Journal of Clinical Oncology, 2005 ASCO Annual Meeting Proceedings, vol. 23, No. 16S, Part I of II (Jun. 1, Supplement), Abstract No. 5011, May 13-17, 2005.

Meco et al., "Effective combination of ET-743 and doxorubicin in sarcoma: preclinical studies," Cancer Chemother. Pharmacol. 52: 131-138 (2003).

Meco et al., "The combination of ET-743 and Irinotecan is active in preclinical models in rhabomyosarcoma," presented at the 16th EORTC-NCI-AARC Symposium on Molecular Targets and Cancer Therapeutics held in Geneva on Sep. 28-Oct. 1, 2004.

Merck Manual on-line edition version, "Types: Overview of Cancer," 4 pages, downloaded from internet website <<http://www.merck.com/mmhe>>, Feb. 2003.

Michaelson, M.D. et al., "Phase II study of three hour, weekly infusion of trabectedin (ET-743) in men with metastatic, androgen-independent prostate carcinoma (AIPC)," Journal of Clinical Oncology, 2005 ASCO Annual Meeting Proceedings, vol. 23, No. 16S, Part I of II (Jun. 1 Supplement), Abstract No. 4517, May 13-17, 2005.

Minuzzo, M. et al., "Interference of Transcriptional Activation by the Antineoplastic Drug Ecteinascidin.743." Proc. Natl. Acad. Sci. USA 97, 6780-4, 2000.

Moore et al., "Sequencing evaluation of ET-743 combinations with standard chemotherapy agents against a panel of human tumor cell lines," Clinical Cancer Research, vol. 6, Abstract 504 (Nov. 2000).

Morioka et al., "Antiangiogenesis Treatment Combined with Chemotherapy Produces Chondrosarcoma Necrosis," Clinical Cancer Research, vol. 9, 1211-1217, Mar. 2003.

Pharma Mar Press Release, "PharmaMar Differs with CPMP Opinion", Pharma Mar Grupo Zeltia, <<http://www.pharmamar.com/en/press/news_release.cfm>>, Jul. 24, 2003.

Pharma Mar Press Release, "PharmaMar Receives EMEA Appeal Decision on Yondelis in Soft Tissue Sarcoma", Pharma Mar Grupo Zeltia, <<http://www.pharmamar.com/en/press/news_release.cfm>>, Nov. 20, 2003.

Pharma Mar Press Release, "Yondelis(r) STS-201 Efficacy and Safety Data Presented at ASCO 2007" Pharma Mar Grupo Zeltia, <<http://www.pharmamar.com/en/press>>, Jun. 5, 2007.

Pharma Mar Press Release, "The European Commission Authorizes Yondelis(r) Commericalization for Soft Tissue Sarcoma" Pharma Mar Grupo Zeltia, <<http://www.pharmamar.com/en/press>>, Sep. 20, 2007.

Pommier, et al., "DNA Sequence- And Structure-Selective Alkylation of Guanine N2 in the DNA Minor Groove by Ecteinascidin 743, a Potent Antitut:I1or Compound from the Caribbean Tunicate Ecteinascidia Turbinata." Biochemistry 35, 13303-9, 1996.

Rinehart, K.L., "Antitumor Compounds from Tunicates." Moo. Res. Rev. 20, 1-27, 2000.

Riccardi et al., "Preclinical Activity and Biodistribution of Ecteinascidin 743 (ET-743) and Doxorubicin (DOX) Combinations in Human Rhabdomyosarcoma," from the AACR-NCI-EORTC Conference on Molecular Targets and Cancer Therapeutics of Oct. 29-Nov. 2, 2001, Abstract 405.

Riccardi et al., "Effective Combinations of ET-743 and Doxorubicin for Tumor Growth Inhibitions Against Murine and Human Sarcomas in Athymic Mice," from the Proceedings of the AACR, vol. 42, Abstract 1132 (Mar. 2001).

Riccardi et al., "Combination of trabectedin and irinotecan is highly effective in a human rhabdomyosarcoma xenograft," Anti-Cancer Drugs, 16:811-815 (2005).

Riofrio, M. et al., "Ecteinascidin-743 (ET-743) 24 hours continuous infusion (CI): Clinical and pharmacokinetic phase I study progressive report," 23rd European Society for Medical Oncology Congress, Abstract 639P, Nov. 6-10, 1998.

Robert et al.,"Pharmacokinetics of Doxorubicin in Sarcoma Patients," Eur. J. Clin. Pharmocol., vol. 31, pp. 695-699, 1987.

Ryan, DP et al., "Phase I and Pharmacokinetic Study of Ecteinascidin-743 Administered as a 72 hours Continuous Intravenous Infusion in Patients with Solid Malignancies", Clinical Cancer Research, vol. 7, pp. 231-242, 2001.

Saito et al.,"Synthesis of Saframycins- 3," J. Org. Chem., 54, 5391, 1989.

Sakai et al., "Additional Antitumor Ecteinascidins from a Caribbean Tunicate: Crystal Structures and Activities in vivo," Proc. Natl. Acad. Sci., vol. 89, Dec. 1992, pp. 11456-11460.

Sato et al., "Multicenter Phase II Trial of Weekly Paclitazel for Advanced or Metastatic Breast Cancer: the Saitama Breast Cancer Clincal Study Group (SBCCSG-01)," Japanese Journal of Clinical Oncology, Vo. 33, No. 8, pp. 371-376, Aug. 2003.

Scotlandi et al., "Effectiveness of Ecteinascidin-743 against Drug-sensitive and—resistant Bone Tumor Cells," Clinical Cancer Research, 8:3893-3903 (Dec. 2002).

Sessa et al., "Trabectedin for Women with Ovarian Carcinoma After Treatment with Platinum and Taxane Fails," Journal of Clinical Oncology, vol. 23,No. 9, pp. 1867-1874, Mar. 20, 2005.

Smyth, "Rationale for Drug Combinations," European Journal of Cancer, 39, 1816-1817 (2003).

Taamma et al., "Phase I Clinical Study of ecteinascidin-743 (ET-743)," Eur. J. Cancer, 33 Suppl. 8, S247-S248, 1997, Abstract.

Taamma, A. et al., "Ecteinascidin-743 (ET-743) 24 hours continuous infusion (CI): clinical and pharmacokinetic phase I study in solid tumor patients (PTS). Preliminary Results" 1998 ASCO Annual Meeting Proceedings, Abstract No. 890, 1998.

Taamma, A. et al., "Phase I clinical study of ecteinascidin-743 (ET-743) as a 24 hours continuous intravenous infusion (CI) in patients (pts) with solid tumors (st): A progress report," ECCO, vol. 9, Abstract No. 1119, Sep. 18, 1997.

Taamma et al., "Phase I and Pharmcokinetic Study of Ecteinascidin-743, a New Marine Compound, Adminstered as a 24 hours Continuous Infusion in Patients with Solid Tumors", J. of Clinical Oncology, vol. 19, No. 5, pp. 1256-1265, 2001.

Tabor et al., "Anti oxidation Potential of Indole Compounds-Structure Activity Studies," Biological Reactive Intermediates IV, p. 833-836, 1990.

Takebayashi et al., "Poisoning of Human DNA Topoisomerase I by Ecteinascidin 743, An Anticancer Drug That Selectively Alkylates DNA in the Minor Groove." Proc. Natl. Acad. Sci. USA 96, 7196-201 1999.

Takahashi et al., "Ecteinascidin 743 (ET-743) and doxorubicin produce synergistic cytotoxic effects in soft tissue sarcoma lines HT-1080 and HS-18," Clinical Cancer Research, vol. 6, Abstract 208 (Nov. 2000).

Takahashi et al., "Sequence-dependent Enhancement of Cytotoxicity Produced by Ecteinascidin 743 (ET-743) with Doxorubicin or Paclitaxel in Soft Tissue Sarcoma Cells," Clinical Cancer Research, 7: 3251-3257 (Oct. 2001).

Ten Hagen et al., "Pegylated Liposomeal Tumor Necrosis Factor-Alpha Results in Reduced Toxicity and Synergistic Antitumor Activity after Systemic Administration in Combination with Liposomeal Doxorubicin (Doxil) in soft tissue Sarcoma-Bearing Rats," Int. J. Cancer, vol. 97, pp. 115-120, 2002.

Twelves et al., "A Phase I and Pharmacokinetic (PK) study of Et-743 evaluating a 3 hours (h) intravenous (iv) infusion (I) in patients (pts) with solid tumors," Clinical Cancer Research, Abstract #307, 5 (11, suppl. 3790S-3791S) 1999.

Twelves, C.J. et al., "Phase I clinical and pharmacokinetic (PK) study of ecteinascidin-743 (ET-743) given as a one hour infusion every 21 days," 1998 ASCO Annual Meeting Proceedings, Abstract No. 889, 1998.

Twelves, C.J. et al., "Phase I and pharmacokinetic study of ecteinascidin-743 (ET-743) given as a one hour infusion every 21 days," ECCO, vol. 9, Abstract No. 1107, Sep. 18, 1997.

Valoti, "Ecteinascidin-743, a New Marine Natural Product with Potent Antitumor Activity on Human Ovarian Carcinoma Xenografts," Clin. Cancer Res., vol. 4, pp. 1977-1983, Aug. 1998.

Valoti, G., et al., "Ecteinascidin-743 (ET-743), a marine natural compound, shows antitumor activity against human ovarian carcinoma xenografts," Novel Therapeutics and Pharmacology, p. S39, Abstract PP179, 1998.

van Kesteren et al. "Clinical Pharmacology of the Novel Marine-derived Anticancer Agent Ecteinascidin 743 Administered as a 1- and 3-h Infusion in a Phase I Study," Anti-Cancer Drugs, vol. 13, No. 4, pp. 381-393, Apr. 2002.

van Kesteren et al. "Yondelis® (trabectedin, ET-743): The Development of an Anticancer Agent of Marine Origin" Anti-Cancer Drugs, vol. 14, No. 7, pp. 487- 502, Aug. 2003.

Villalona-Calero, M. et al., "A phase I and pharmacokinetic study of ET-743, a novel DNA minor groove binder of marine origin, administered as a 1-hour infusion daily × 5 days," Annals Oncology, Abstract 453, 1998.

Villalona-Calero, M. et al., "Final results of a Phase I and pharmacokinetic (PK) study of the marine minor groove binder ET-743 on a daily × 5 schedule,"1999 ASCO Annual Meeting Proceedings, Abstract No. 691, 1999.

Wiesenthal, "Is one 'sensitive' drug better than another?" downloaded from internet website <<http://weisenthal.org/feedback.html>>, Feb. 4, 2002.

Wright et al., "Antitumor Tetrahydroisoquinonline Alkaloids from the Colonial Ascidian Ecteinascidia Turbinata", J. Org. Chem., vol. 55, pp. 4508-4512, 1990.

Zewail-Foote, et al., "Ecteinascidin 743: A Minor Groove Alkylator that Bends DNA Toward the Major Groove," J. Med. Chem. 42, 2493-7, Jul. 15, 1999.

Bernacki et al., "In Vitro Antitumor Activity of 9-Nitro-Camptothecin as a Single Agent and in Combination with other Antitumor Drugs" Annals of the New York Academy of Sciences, vol. 922 (1), p. 293, Dec. 2000.

Delaloge et al., "Ecteinascidin (ET-743) in heavily pretreated refractory sarcomas: Preliminary evidence of activity," Eur. J. Cancer, vol. 35, suppl. 4, p. S271, Abstract No. 1080, Sep. 15, 1999.

D'Incalci et al., "Mode of action of Ecteinascidin-743 (ET-743)," Proceedings of the 1999 AACR-NCI-EORTC International Conference, Clinical Cancer Research, vol. 5, Supplement, pp. 3872s-3873s, Abstract of Plenary Session 7, Nov. 16-19, 1999.

European Medicines Agency (EMEA), "Scientific Discussion" from the European Public Assessment Report for Yondelis®, Revision 1, published Mar. 31, 2008, downloaded from the internet on Apr. 2, 2008, from the website <<http://www.emea.europa.eu/humandocs/Humans/EPAR/yondelis/yondelis.htm>>.

Garcia-Carbonero et al., "Population pharmacokinetics of ecteinascidin 743 in patients with advanced soft tissue sarcoma," Clinical Cancer Research, vol. 6, Supplement, Abstract 211, p. 4508s, NCI-EORTC-AACR Symposium On New Drugs In Cancer Therapy, Nov. 7-10, 2000.

Giovanna et al., "Importance of DNA repair mechanisms for the sensitivity of tumor cells to ET-743," Proceedings of the 1999 AACR-NCI-EORTC International Conference, Clinical Cancer Research, vol. 5, Supplement, p. 3790s, Abstract 303, Nov. 16-19, 1999.

Hoekman at al., "A phase I/II study of dose-escalated docetaxel given two weekly in combination with a fixed dose of G-CSF," European Journal of Cancer, vol. 37, p. S76, Abstract 270, Oct. 22, 2001.

Hornicek et al., "In vitro effect of the tetrahydroisoquinoline alkaloid Ecteinascidin-743 (ET-743) on chondrosarcoma (CHSA) cells," Proceedings of the 1999 AACR-NCI-EORTC International Conference, Clinical Cancer Research, vol. 5, Supplement, p. 3790s, Abstract 304, Nov. 16-19, 1999.

Jimeno et al., "Pharmacokinetics (PK)/Pharmacodynamic (PD) Relationships in Patients (PT) Treated With Ecteinascidin-743 (ET-743) Given As 24 Hours Continuous Infusion (CI)," Journal of Clinical Oncology, ASCO Annual Meeting Proceedings, Abstract No. 744, May 15-18, 1999.

Jin et al., "The antitumor agent Ecteinascidin 743 (ET743), inhibits transcriptional activation of the MDR1 Gene by multiple inducers,"

Proceedings of the 1999 AACR-NCI-EORTC International Conference, Clinical Cancer Research, vol. 5, Supplement, p. 3790s, Abstract 302, Nov. 16-19, 1999.

Lopez-Lazaro et al., "Exploratory evaluation of the potential predictors for dose-limiting toxicities (DLTs) in patients treated with Ecteinascidin-743 (ET-743) as a 24-h intravenous (iv) infusion every 3 weeks and its relationship to pharmacokinetics (PK)," Proceedings of the 1999 AACR-NCI-EORTC International Conference, Clinical Cancer Research, vol. 5, Supplement, p. 3791s, Abstract 308, Nov. 16-19, 1999.

Michaelson et al., "A Phase I Study of 9-Nitrocamptothecin Given Concurrently with Capecitabine in Patients with Refractory, Metastatic Solid Tumors," Cancer, vol. 97 (1), pp. 148-154, Jan. 1, 2003.

Rosing et al., "Pharmacokinetics (PK) of Ecteinascidin-743 (Et-743) in three different phase I trials," Proceedings of the American Association for Cancer Research, vol. 40, pp. 81, abstract No. 542, Mar. 1999.

Ryan, D.P. "Studies with Ecteinascidin-743 (ET-743) A Marine Alkaloid," Cancer Invest, vol. 18 (suppl 1), pp. 112, abstract No. 87, Jan. 2000, from the Chemotherapy Foundation Symposium XVII Innovative Cancer Therapy for Tomorrow, Nov. 3-6, 1999, New York, NY.

Scotto et al., "Ecteinascidin 743, a novel chemotherapeutic agent that targets transcriptional activation of a subset of genes, including MDR1," Clinical Cancer Research, vol. 6, Supplement, Abstract 210, p. 4508s, NCI-EORTC-AACR Symposium On New Drugs In Cancer Therapy, Nov. 7-10, 2000.

Shertzer et al., "Protection Against Carbon Tetrachloride Hepatoxicity by Pretreatment with indole-3-carbinol," Exptl. Molec. Pathol., vol. 46, pp. 180-189 (1987).

Shertzer et al., "Protection from N-Nitrosodimethylamine Mediated Liver Damage by Indole-3-carbinol," Exptl. Molec. Pathol., vol. 47, pp. 211-218 (1987).

Taamma et al., "Ecteinascidin-743 (ET-743) 24 hour continuous intravenous infusion (CI) phase I study in solid tumors (ST) patients (pts)." Proceedings of the American Association for Cancer Research, vol. 39, pp. 323, abstract No. 2207, Mar. 1998.

Taamma et al., "Ecteinascidin-743 (ET-743) in heavily pretreated refractory sarcomas: early results of the French experience," Proceedings of the 1999 AACR-NCI-EORTC International Conference, Clinical Cancer Research, vol. 5, Supplement, p. 3791s, Abstract 309, Nov. 16-19, 1999.

Takebayashi et al., "Multidrug Resistance Induced by DNA Minor Groove Alkylation of Ecteinascidin 743 (Et743)," Proceedings of the 1999 AACR-NCI-EORTC International Conference, Clinical Cancer Research, vol. 5, Supplement, p. 3851s, Abstract 602, Nov. 16-19, 1999.

Takebayashi et al., "Nucleotide excision repair-dependent cytotoxicity of Ecteinascidin 743," Clinical Cancer Research, vol. 6, Supplement, Abstract 207, p. 4508s, NCI-EORTC-AACR Symposium On New Drugs In Cancer Therapy, Nov. 7-10, 2000.

Ten Hagen et al., "Pegylated Liposomal Tumor Necrosis Factor-Alpha Results in Reduced Toxicity and Synergistic Antitumor Activity after Systemic Administration in Combination with Liposomal Doxorubicin (Doxil) in soft tissue Sarcoma-Bearing Rats," Int. J. Cancer, vol. 97, pp. 115-120, 2002.

Twelves et al., "Phase I Trials with ET-743, a marine derived (MD) anticancer agent," Eur. J. Cancer, vol. 35, suppl. 4, p. S283, Abstract No. 1135, Sep. 15, 1999.

Twelves et al., "Phase I and pharmacokinetic study of YondelisTM (Ecteinascidin-743; ET-743) administered as an infusion over 1 h or 3 h every 21 days in patients with solid tumours," European Journal of Cancer, vol. 39, p. 1842-1851, 2003; available online Aug. 14, 2003.

Weiwei et al., "Potent antitumor activity of ET-743 against human soft tissue sarcoma cell lines," Proceedings of the 1999 AACR-NCI-EORTC International Conference, Clinical Cancer Research, vol. 5, Supplement, p. 3790s, Abstract 305, Nov. 16-19, 1999.

Zelek et al., "Preliminary results of phase II study of ecteinascidin (ET-743) with the 24 hour (H) continuous infusion (CI) q3week schedule in pretreated" Clinical Cancer Research, vol. 6, Supplement, Abstract 212, pp. 4508s-4509s, NCI-EORTC-AACR Symposium On New Drugs In Cancer Therapy, Nov. 7-10, 2000.

Alexopoulos, "Phase II study of pegylated liposomal doxorubicin (Caelyx(R)) and docetaxel as first-line treatment in metastatic breast cancer," Ann. Oncol., 2004, 15(6):891-5.

D'Incalci et al., "Unique Features of the Mode of Action of ET-743", The Oncologist, 7, p. 210-216, Jun. 2002.

Gourley C. et al., "Malignant mixed Mesodermal Tumours—Biology and Clinical Aspects," European Journal of Cancer 2002, vol. 38, No. 11, pp. 1437-1446.

Halm et al., "A phase II study of pegylated liposomal doxorubicin for treatment of advanced hepatocellular carcinoma," Ann. Oncol., 2000, 11(1):113-114.

Puchalski et al., "Pharmacokinetics of Ecteinascidin 743 Administered as a 24-h Continuous Intravenous Infusion to Adult Patients with Soft Tissue Sarcomas associations with Clinical Characteristics, Pathophysiological Variables and Toxicity," Cancer Chemotherapy and Pharmacology, 2002, vol. 50, No. 4, pp. 309-319.

Rote Liste 2002 "Doxorubicin," entries 86-056 through 86-062, 2002.

Schwartsmann G. et al., "Marine Organisms as a Source of New Anticancer Agents," The Lancet Oncology, 2001, vol. 2, No. 4, pp. 221-225.

Wollina, "Multicenter study of pegylated liposomal doxorubicin in patients with cutaneous T-cell lymphoma," Cancer 2003, 1:98(5):993-1001, published online Jul. 24, 2003.

Donald et al, "Comparison of four modulators of drug metabolism as protectants against the hepatotoxicity of the novel antitumor drug yondelis (ET-743) in the female rat and in hepatocytes in vitro," Cancer Chemother Pharmacol, Apr. 2004, vol. 53, pp. 305-312.

Forouzesh et al., Proc. Am. Soc. Clin. Oncol. ASCO meeting, Abstract 373, Jun. 3, 2001, Internet Archive Entry from the website <<http://web.archive.org/webr/*/http://www.asco.org/>>, 32 pages.

Horstmann et al., "Risks and Benefits of Phase I Oncology Trials, 1991 through 2002," New England Journal of Medicine, vol. 352, pp. 895-904; Mar. 3, 2005.

Lau et al., "A Phase I and Pharmacokinetic Study of Ecteinascidin-743 (Yondelis) in Children with Refractory Solid Tumors." Clinical Cancer Research, vol. 11, pp. 672-677, Jan. 15, 2005.

PR Newswire, PR Newswire, Oct. 14, 2001, 4 pages.

Sarosy et al., "Phase I Study of α2-interferon plus Doxorubicin in Patients with Solid Tumors," Cancer Research, vol. 46, pp. 5368-5371, 1986.

* cited by examiner

COMBINATION OF ET-743 AND A 5-FLUOROURACIL PRO-DRUG FOR CANCER TREATMENT

The invention relates to a combination of medicaments, more particularly a combination of medicaments for use in the treatment of cancer.

FIELD OF THE INVENTION

The present invention is directed to the use of ecteinascidin 743 in combination with another active drug for the treatment of cancer.

BACKGROUND OF THE INVENTION

Cancer comprises a group of malignant neoplasms that can be divided into two categories, carcinoma, comprising a majority of the cases observed in the clinics, and other less frequent cancers, which include leukemia, lymphoma, central nervous system tumors and sarcoma. Carcinomas have their origin in epithelial tissues while sarcomas develop from connective tissues and those structures that had their origin in mesoderm tissues. Sarcomas can affect, for instance, muscle or bone and occur in the bones, bladder, kidneys, liver, lung, parotid, spleen, etc.

Cancer is invasive and tends to metastasise to new sites. It spreads directly into surrounding tissues and also may be disseminated through the lymphatic and circulatory systems.

Many treatments are available for cancer, including surgery and radiation for localised disease, and drugs. However, the efficacy of available treatments on many cancer types is limited, and new, improved forms of treatment showing clinical benefit are needed.

This is especially true for those patients presenting with advanced and/or metastatic disease. It is also true for patients relapsing with progressive disease after having been previously treated with established therapies for which further treatment with the same therapy is mostly ineffective due to acquisition of resistance or to limitations in administration of the therapies due to associated toxicities.

Chemotherapy plays a significant part in cancer treatment, as it is required for treatment of advanced cancers with distant metastasis and often helpful for tumor reduction before surgery. Many anti-cancer drugs have been developed based on various modes of action.

The most commonly used types of anticancer agents include: DNA-alkylating agents (for example, cyclophosphamide, ifosfamide), antimetabolites (for example, methotrexate, a folate antagonist, and 5-fluorouracil, a pyrimidine antagonist), microtubule disrupters (for example, vincristine, vinblastine, paclitaxel), DNA intercalators (for example, doxorubicin, daunomycin, cisplatin), and hormone therapy (for example, tamoxifen, flutamide). The ideal antineoplastic drug would kill cancer cells selectively, with a wide therapeutic index relative to its toxicity towards non-malignant cells. It would also retain its efficacy against malignant cells, even after prolonged exposure to the drug.

Unfortunately, none of the current chemotherapies possess an ideal profile. Most possess very narrow therapeutic indexes and, in practically every instance, cancerous cells exposed to slightly sublethal concentrations of a chemotherapeutic agent will develop resistance to such an agent, and quite often cross-resistance to several other antineoplastic agents.

The ecteinascidins (herein abbreviated ETs) are exceedingly potent antitumor agents isolated from the marine tunicate *Ecteinascidia turbinata*. Several ecteinascidins have been reported previously in the patent and scientific literature. See, for example U.S. Pat. No. 5,089,273, which describes novel compounds extracted from the tropical marine invertebrate, *Ecteinascidia turbinata*, and designated therein as ecteinascidins 729, 743, 745, 759A, 759B and 770. These compounds are useful as antibacterial and/or antitumor agents in mammals. U.S. Pat. No. 5,478,932 describes ecteinascidins isolated from the Caribbean tunicate *Ecteinascidia turbinata*, which provide in vivo protection against P388 lymphoma, B16 melanoma, M5076 ovarian sarcoma, Lewis lung carcinoma, and the LX-1 human lung and MX-1 human mammary carcinoma xenografts.

One of the ETs, ecteinascidin-743 (ET-743), is a novel tetrahydroisoquinoline alkaloid with considerable antitumor activity in murine and human tumors in vitro and in vivo, and is presently in clinical trials. ET-743 possesses potent antineoplastic activity against a variety of human tumor xenografts grown in athymic mice, including melanoma and ovarian and breast carcinoma.

A clinical development program of ET-743 in cancer patients was started with phase I studies investigating 1-hour, 3-hour, 24-hour and 72-hour intravenous infusion schedules and a 1 hour daily×5 (d×5) schedule. Promising responses were observed in patients with sarcoma and breast and ovarian carcinoma. Therefore this new drug is currently under intense investigation in several phase II clinical trials in cancer patients with a variety of neoplastic diseases. Further detail on the use of ET-743 for the treatment of the human body for cancer is given in WO 0069441, incorporated herein by reference in its entirety.

A recent review of ET-743, its chemistry, mechanism of action and preclinical and clinical development can be found in van Kesteren, Ch. et al., 2003, *Anti-Cancer Drugs*, 14 (7), pages 487-502: "Yondelis (trabectedin, ET-743): the development of an anticancer agent of marine origin", and references therein.

Combination therapy using drugs with different mechanisms of action is an accepted method of treatment which helps prevent development of resistance by the treated tumor. In vitro activity of ET-743 in combination with other anticancer agents has been studied, see for example WO 02 36135, incorporated herein by reference in its entirety.

It is an object of the invention to provide an efficacious combination product for treatment of cancer. More particularly, an object of this invention is an effective cancer combination therapy.

SUMMARY OF THE INVENTION

According to the present invention, we provide a combination therapy for the treatment of cancer which employs ecteinascidin 743 and 5-fluorouracil. Typical dosing protocols for the combination therapy are provided, where the 5-fluorouracil is given in the form of a pro-drug, especially an oral pro-drug exemplified by capecitabine (Xeloda®). From phase I clinical trials, we have determined that a combination of ET-743 and capecitabine is tolerable and feasible, with evidence of antitumor activity.

We also provide a method of treating a cancer patient, which comprises administering ET-743 and a pro-drug of 5-fluorouracil, notably capecitabine. The ET-743 and pro-drug of 5-fluorouracil are preferably administered sequentially, with multiple oral administrations of the pro-drug of 5-fluorouracil following infusion of ET-743.

We further provide the use of ET-743 in the preparation of a medicament for carrying out the method of treatment. We also provide the use of the pro-drug of 5-fluorouracil, notably capecitabine, in the preparation of a medicament for carrying out the method of treatment. We provide the use of ET-743 and the pro-drug of 5-fluorouracil, notably capecitabine, in the preparation of a medicament for carrying out the method of treatment.

DETAILED DESCRIPTION

ET-743 is a natural compound represented by the following formula:

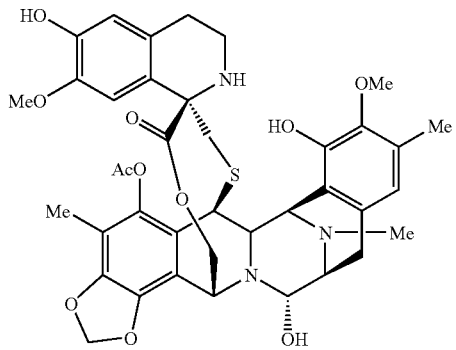

As used herein, the term "ET-743" also covers any pharmaceutically acceptable salt, ester, solvate, hydrate or a pro-drug compound which, upon administration to the recipient is capable of providing (directly or indirectly) the compound ET-743. The preparation of salts and other derivatives, and prodrugs, can be carried out by methods known in the art.

ET-743 is typically supplied and stored as a sterile lyophilized product, with ET-743 and excipient in a formulation adequate for therapeutic use, in particular a formulation containing mannitol and a phosphate salt buffered to an adequate pH.

It is currently preferred to administer the ET-743 by infusion. The infusing step is typically repeated on a cyclic basis, which may be repeated as appropriate over for instance 1 to 35 cycles. The cycle includes a phase of infusing ET-743, and usually also a phase of not infusing ET-743. Typically the cycle is worked out in weeks, and thus the cycle normally comprises one or more weeks of an ET-743 infusion phase, and one or more weeks to complete the cycle. In one embodiment a cycle of 3 weeks is preferred, alternatively it can be from 2 to 6 weeks. The infusion phase can itself be a single administration in each cycle of say 1 to 72 hours, more usually of about 1, 3 or 24 hours, or infusion on a daily basis in the infusion phase of the cycle for preferably 1 to 5 hours, especially 1 or 3 hours. Thus, for example, the EIT743 might be administered on each of the first five days of a 3 week cycle. We currently prefer a single administration at the start of each cycle. Preferably the infusion time is about 1, 3 or 24 hour. In one embodiment an infusion time of about 3 hours is preferred.

The dose will be selected according to the dosing schedule, having regard to the existing data on Dose Limiting Toxicity, on which see for example the incorporated WO patent specifications, and also see van Kesteren, Ch. et al., 2003, Anti-Cancer Drugs, 14 (7), pages 487-502: "Yondelis (trabectedin, ET-743): The development of an anticancer agent of marine origins". This article is incorporated herein in full by specific reference.

For a single administration of ET-743 at the start of each cycle, we prefer a dose in the range 0.2 to 2 mg/m², more preferably 0.4 to 1.5 mg/m², and most preferably 0.7 to 1.2 mg/m². More generally, for other cycles which involve a single administration at intervals of 1 week or more, the amount of ET-743 is ordinarily in the range 0.7 to 1.2 mg/m². Lower amounts are suitable where there is repeat dosing on a daily schedule.

Most preferably, the ET-743 is given by infusion at a dose of about 0.75 mg/m²-1.4 mg/m², preferably about 0.9 mg/m²-1.2 mg/m², most preferably about 0.75 mg/m² or about 0.9 mg/m² on day 1 of a 3 week cycle.

As noted in the incorporated article by van Kesteren, the combination of ET-743 with dexamethasone gives unexpected advantages. It has a role in hepatic prophylaxis. We therefore prefer to administer dexamethasone to the patient, typically at around the time of infusing the ET-743. For example, we prefer to give dexamethasone on the day before ET-743, and/or the day after ET-743. The administration of dexamethasone can be extended, for example to more than one day following ET-743. In particular, we prefer to give dexamethasone at days —1, 2, 3 and 4 relative to a single administration of ET-743 on day 1 of a cycle.

The ET-743 is administered as part of a combination therapy with a pro-drug of 5-fluorouracil, preferably capecitabine.

Capecitabine is of the formula:

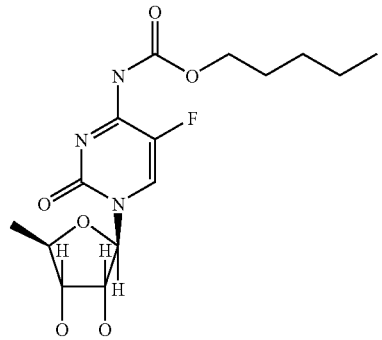

Capecitabine is indicated for the treatment of certain cancers. Information is available on the website www.xeloda.com, and the extensive scientific literature on capecitabine. Capecitabine is a pro-drug which is readily absorbed from the gastrointestinal tract. In the liver, a 60 kDa carboxylesterase hydrolyses much of the compound to 5'-deoxy-5-fluorocytidine (5'-DFCR). Cytidine deaminase, an enzyme found in most tissues, including tumors, subsequently converts 5'-DFCR to 5'-deoxy-5-fluorouridine (5'-DFUR). The enzyme thymidine phosphorylase (dThdPase) then hydrolyses 5'-DFUR to the active drug 5-fluorouracil (5-FU). Many tissues throughout the body express thymidine phosphorylase. Some human carcinomas express this enzyme in higher concentrations than surrounding normal tissues.

Capecitabine is administered orally as part of the cycle of treating the patient. In the present invention we prefer repeat doses on a daily basis as part of the cycle. We prefer that capecitabine is given for a majority of the days of the cycle, for example for about ⅔, ¾ or some other fraction of the cycle. For a cycle of 3 weeks, we prefer administration for 14 days, especially days 2 to 15 of a 3 week cycle. Other administration protocols can be designed having regard to this embodiment. In general, capecitabine is not given on a day when ET-743 is administered, and preferably commencement of administration of capecitabine is on a day after ET-743 administration.

In one embodiment the dosage amount of capecitabine is preferably in the range from 500 to 3000 mg/m$^2$/day, more preferably 1500 to 2500 mg/m$^2$/day, and even most preferably a dose of about 1500 mg/m$^2$/day, about 1600 mg/m$^2$/day or about 2000 mg/m$^2$/day. This dosage can be administered in fractions, for example in a twice-daily regimen.

Most preferably, the capecitabine is given orally at a dose of about 1500 mg/m$^2$/day, about 1600 mg/m$^2$/day or about 2000 mg/m$^2$/day on days 2 to 15 of each cycle.

Other pro-drugs of 5-fluorouracil can be employed in place of capecitabine. Such pro-drugs include other compounds which metabolise to 5'-deoxy-5-fluorouridine, and thence to 5-fluorouracil. For example, reference is made to U.S. Pat. No. 4,996,891 to Fujiu et al., and U.S. Pat. No. 5,472,949 to Arasaki et al. The patents are incorporated herein in full by specific reference. In particular, for the present invention, we prefer that the pro-drug is a compound of claim 1 of U.S. Pat. No. 4,966,891 or a compound of claim 1 of U.S. Pat. No. 5,472,949.

Depending on the type of tumor and the developmental stage of the disease, the treatments of the invention are useful in preventing the risk of developing tumors, in promoting tumor regression, in stopping tumor growth and/or in preventing metastasis. In particular, the method of the invention is suited for human patients, especially those who are relapsing or refractory to previous chemotherapy. First line therapy is also envisaged.

Preferably, the combination therapy is used according to the above schedules and dosages for the treatment of sarcoma, osteosarcoma, ovarian cancer, breast cancer, melanoma, vaginal cancer, gastric cancer, adenocarcinoma, colorectal cancer, mesothelioma, renal cancer, endometrial cancer and lung cancer. Most preferably the patients are breast cancer patients.

In a further aspect of the present invention, a medical kit for administering ET-743 in combination with a pro-drug of 5-fluorouracil is provided, comprising printed instructions for administering ET-743 according to the dosing schedules set forth above, and a supply of ET-743 in dosage units for at least one cycle, wherein each dosage unit contains the appropriate amount of ET-743 for the treatments as defined above and a pharmaceutically acceptable carrier.

Although guidance for the dosage is given above, the correct dosage of the compounds will vary according to the particular formulation, the mode of application, and the particular situs, host and tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

EXAMPLE

Phase I Clinical Trial

The objective of this study was to determine the maximum tolerated dose (MTD) of the combination of ET-743 administered over 3 hours intravenously on Day 1 and capecitabine orally administered twice daily on Days 2-15. An additional objective was to evaluate the safety profile of this regimen.

The patients' enrolment to the study was carried out according to the standard inclusion criteria, including creatinine and liver function tests within normal limits and ECOG performance status 0-1. In addition, standard exclusion criteria were also followed including known CNS metastasis and peripheral neuropathy>grade 1.

Dose-limiting toxicity (DLT) was defined as:

Grade 3-4 non-hematologic toxicity, excluding nausea & vomiting (N/V) in the absence of optimal supportive care, grade 3 transaminitis<7 days, and hand-foot syndrome.

Grade 4 neutropenia×5 days or with fever/sepsis.

Treatment delay of more than 21 days.

Platelets<25,000.

Drug administration was conducted on 21-day cycles. ET-743 was administered as a 3-hour infusion i.v. on day 1 of each cycle (every 3 weeks). Dexamethasone was administered from day −1 to day 3. Capecitabine was orally administered twice-daily on days 2-15 every 3 weeks. In addition, capecitabine was administered at the fixed dose of 2000 mg/m$^2$/day, while ET-743 was started at 400 μg/m$^2$ and escalated thereafter in subsequent cohorts of at least 3 new cases.

Table 1 shows the patient characteristics.

TABLE 1

| | |
|---|---|
| Number of patients (courses) | 14 (50) |
| Median courses/patient (range) | 2 (1-10) |
| Male:female | 5:9 |
| PS 0:1 | 3:11 |
| Median age (range) | 52 (19-70) |
| Prior chemotherapy (none) | 13 (1) |
| Tumor types | |
| sarcoma | 7 |
| breast, ovarian, cervical, cholangiocarcinoma, gastric, melanoma, vaginal, adenocarcinoma | 1 each |

Table 2 shows the number of patients exposed in each dose escalation level and the dose limiting toxicities observed.

TABLE 2

| Cohort | ET-743 (mg/m$^2$) | Capecitabine (mg/m$^2$) | # Patients | # cycles |
|---|---|---|---|---|
| 1 | 0.4 | 2000 | 3 | 13 |
| 2 | 0.6 | 2000 | 6* | 23 |
| 3 | 0.75 | 2000 | 3 | 10 |
| 4 | 0.9 | 2000 | 2** | 4 |

*DLT: grade 3 mucositis and febrile neutropenia
**DLT: grade 3 nausea and dehydration Table 3 shows the frequently reported drug-related hematologic toxicities. In order to define the toxicity grade, NCI common criteria is used.

TABLE 3

| | Grade/Number of Cycless | |
|---|---|---|
| | 3 | 4 |
| Neutropenia | 2 | 1 |
| Thrombocytopenia | 0 | 0 |
| Anemia | 1 | 0 |

(Total Courses Administered: 50)

Table 4 shows the frequently reported drug-related non-hematologic toxicities. In order to define the toxicity grade, NCI common criteria is used.

TABLE 4

| | Grade/Number of Cycles | | | |
|---|---|---|---|---|
| | 1 | 2 | 3 | 4 |
| Nausea/Vomiting | 25/11 | 0 | 4/2 | 0 |
| Fatigue | 15 | 7 | 1 | 0 |
| Transaminitis | 29 | 7 | 0 | 0 |
| Hand-Foot Syndrome | 10 | 9 | 2 | 0 |
| Diarrhea/Constipation | 8/13 | 1/3 | 4/0 | 0 |
| Alk Phos/Bilirubin | 11/6 | 1/5 | 0 | 0 |
| Mucositis | 4 | 1 | 1 | 0 |

(Total Courses Administered: 50)

Regarding the antitumoral activity of the combination, 13 of 14 patients were evaluable for response (1 patient were removed from study for toxicity after 1 cycle). Seven patients (4 sarcoma, 1 each gastric, breast, vaginal, adenocarcinoma) had stable disease after 10, 6, 5, 2, 3, 4, and 3 cycles. One patient with cholangiocarcinoma had a partial response after 8 cycles. Five patients progressed after 1-2 cycles

The invention claimed is:

1. A method of treating a human body having cancer comprising administering an effective therapeutic amount of ET-743 in combination with an effective therapeutic amount of a 5-fluorouracil pro-drug.

2. The method according to claim 1, wherein ET-743 is administered in combination with capecitabine.

3. The method according to claim 2, wherein capecitabine and ET-743 are provided as separate medicaments for administration at different times.

4. The method according to claim 3, wherein capecitabine is administered in a dose range between 1500 to 2500 mg/m²/day.

5. The method according to claim 3, wherein ET-743 is administered in a dose range between 0.75 and 1.4 mg/m².

6. The method according to claim 4 or 5, wherein capecitabine is administered in a dosage of up to 2000 mg/m²/day and ET-743 is administered in a dosage of up to 1.2 mg/m².

7. The method according to claim 6, wherein capecitabine is administered in a dosage about 1600 mg/m²/day and ET-743 is administered in a dosage about 0.9 mg/m².

8. The method according to claim 4 or 5, wherein capecitabine is orally administered.

9. The method according to claim 8, wherein ET-743 is administered by intravenous injection.

10. The method according to claim 9, wherein the infusion time for intravenous injection of ET-743 is up to 24 hours.

11. The method according to claim 10, wherein the infusion time for intravenous injection of ET-743 is about 3 hours for ET-743.

12. The method according to claim 9, where the infusions of ET-743 are carried out at an interval of 1 to 6 weeks.

13. The method according to claim 12, wherein the infusion of ET-743 is carried out once every 21 days.

14. The method according to claim 13, wherein the infusion of ET-743 is carried out on day 1 and the administration of capecitabine from days 2 to 15, every 21 days.

15. The method according to claim 14, wherein capecitabine is administered twice-daily.

16. A method according to claim 1, in which the patient has a cancer selected from sarcoma, osteosarcoma, ovarian cancer, breast cancer, melanoma, vaginal cancer, colorectal cancer, gastric cancer, adenocarcinoma, mesothelioma, renal cancer, endometrial cancer, cholangiocarcinoma and lung cancer.

17. A method according to claim 16, in which the patient has a cancer selected from sarcoma, breast cancer, gastric cancer, vaginal cancer, cholangiocarcinoma and adenocarcinoma.

18. A medical kit for administering ET-743 in combination with capecitabine, comprising a supply of ET-743 in dosage units for at least one cycle, wherein each dosage unit contains the appropriate amount of ET-743 for the treatments and a pharmaceutically acceptable carrier, and printed instructions for administering ET-743 according to a dosing schedule.

19. The method according to claim 4, wherein capecitabine is administered in a dosage of about 2000 mg/m²/day.

20. The method according to claim 4, wherein capecitabine is administered in a dosage of about 1600 mg/m²/day.

21. The method according to claim 5, wherein ET-743 is administered in a dose range between 0.9 and 1.2 mg/m².

22. The method according to claim 5, wherein ET-743 is administered in a dosage of about 0.9 mg/m².

23. The method according to claim 5, wherein ET-743 is administered in a dosage of about 0.9 mg/m² on day 1 of a 3 week cycle.

24. The method according to claim 2, wherein capecitabine is administered in a dosage of about 1600 mg/m²/day and ET-743 is administered in a dosage range between 0.9 and 1.2 mg/m².

25. The method according to claim 24, wherein the infusion of ET-743 is carried out on day 1 and the administration of capecitabine from days 2 to 15, every 21 days.

26. The method according to claim 9, wherein commencement of administration of capecitabine is on a day after ET-743 administration.

* * * * *